US008968266B2

(12) United States Patent
Kumar

(10) Patent No.: US 8,968,266 B2
(45) Date of Patent: Mar. 3, 2015

(54) SANITARY UNDERGARMENT

(76) Inventor: Deepa A. Kumar, Bangalore (IN)

( * ) Notice: Subject to any disclaimer, the term of this patent is extended or adjusted under 35 U.S.C. 154(b) by 591 days.

(21) Appl. No.: 13/321,945

(22) PCT Filed: Jan. 25, 2010

(86) PCT No.: PCT/IN2010/000042
§ 371 (c)(1),
(2), (4) Date: Nov. 22, 2011

(87) PCT Pub. No.: WO2010/137030
PCT Pub. Date: Dec. 2, 2010

(65) Prior Publication Data
US 2012/0071849 A1    Mar. 22, 2012

(30) Foreign Application Priority Data

May 26, 2009    (IN) ............................ 1218/CHE/2009

(51) Int. Cl.
*A61F 13/15*    (2006.01)
(52) U.S. Cl.
USPC ........... 604/396; 604/367; 604/360; 604/359; 604/385.24; 604/385.28
(58) Field of Classification Search
USPC ........ 604/396, 367, 360, 359, 385.24, 385.28
See application file for complete search history.

(56) References Cited

U.S. PATENT DOCUMENTS

| | | | |
|---|---|---|---|
| 5,360,422 A * | 11/1994 | Brownlee et al. | ........ 604/385.15 |
| 6,041,446 A * | 3/2000 | Braunstein et al. | ............... 2/400 |
| 6,558,364 B1 | 5/2003 | Santa Cruz et al. | |
| 6,986,762 B2 | 1/2006 | Wada et al. | |
| 2005/0065494 A1 | 3/2005 | Harriott | |
| 2005/0197643 A1 | 9/2005 | Suga et al. | |

* cited by examiner

*Primary Examiner* — Jacqueline F. Stephens
(74) *Attorney, Agent, or Firm* — Economou IP Law; Vangelis Economou

(57) ABSTRACT

A sanitary undergarment, comprising a fabric body, a crotch portion, a waist opening, and a thigh opening, each comprising one or more layers made of a breathable leak-proof material for blocking flow of the body fluid through the fabric body. The sanitary undergarment generally comprises a boxer brief construction. The fabric body constitutes a front portion and a rear portion and blocks flow of the body fluid of the wearer outside the sanitary undergarment and prevents staining of the outer garment. The front portion covers a front part of a pelvic region of the wearer. The rear portion covers a rear part of the pelvic region of the wearer. The crotch portion covers a crotch region of the wearer and comprises one or more of a first layer and a second layer. The second layer prevents chafing at the inner thigh regions of the wearer.

21 Claims, 17 Drawing Sheets

SANITARY UNDERGARMENT

CROSS REFERENCE TO RELATED APPLICATIONS

This application claims the benefit of non-provisional patent application number 1218/CHE/2009 titled "Sanitary Undergarment", filed on May 26, 2009 in the Indian Patent Office.

BACKGROUND

This invention, in general, relates to undergarments. More particularly, this invention relates to a sanitary undergarment for blocking flow of body fluid outside the sanitary undergarment for preventing staining of an outer garment.

Women generally menstruate once a month for a period of three to seven days. During the menstrual period, women typically use either sanitary pads or tampons to absorb menstruation fluid and to prevent staining of garments. Women typically wear undergarments not designed for menstruation. Some available undergarments are provisioned for accommodating the sanitary pads or the tampons. However, both the sanitary pads and the tampons do not prevent staining of the undergarments and hence the outer garment. Typically, staining of the undergarment occurs for two reasons. The tampons or the sanitary pads when used for a long time get soaked completely and do not absorb the menstrual fluid and stain the undergarment and hence the outer garment. With use of sanitary pads, the staining generally occurs at front of the undergarment, back of the undergarment, or the sides of undergarment near the inner thigh regions. Staining is higher at the inner thigh region if the sanitary pad does not have wings. Staining is largely reduced if the sanitary pads have wings. However, the sanitary pads with wings cause chafing at the inner thigh region of the wearer due to friction.

Furthermore, the tampons or the sanitary pads when worn improperly or due to common physical movements of the wearer, for example, sitting, walking, sleeping, etc, are not held securely to the undergarment and result in staining of the undergarment. Typically, women wear regular undergarments during the menstrual period. The regular undergarment does not provide the required protection from staining. The stained undergarment further stains an outer garment worn by women. Furthermore, the sanitary undergarments available today are made of plastic materials and non-breathable materials and hence are uncomfortable to wear. The undergarments made of non-breathable materials increase the risk of rashes and skin problems for women wearing the undergarments. Moreover, the undergarments made of the non-breathable materials create a bad odor. Furthermore, design of the undergarment typically used by women, is not suitable for preventing leaks in susceptible areas and thereby stains both the undergarment and the outer garment worn by women.

Hence, there is an unmet need for a sanitary undergarment made of breathable materials. Moreover, there is an unmet need for a sanitary undergarment designed to prevent leakage of the menstrual fluid from any portion of the sanitary undergarment and to prevent staining of the outer garment worn by women. Furthermore, there is an unmet need for a sanitary undergarment allowing air permeability, maintaining dryness, and preventing odor, rashes and infections.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The sanitary undergarment disclosed herein addresses the above stated need for a sanitary undergarment made of breathable materials. Furthermore, the sanitary undergarment disclosed herein addresses the need for a sanitary undergarment designed to prevent leakage of a body fluid of a wearer through any portion of the sanitary undergarment and to prevent staining of an outer garment. The sanitary undergarment is washable and reusable. The sanitary undergarment is used along with, for example, an absorbent pad, a tampon, reusable fabric pads, menstrual cups and any other form of hygiene product.

The sanitary undergarment disclosed herein comprises a fabric body, a crotch portion, a waist opening, and thigh openings. The fabric body comprises a front portion and a rear portion, wherein the front portion and the rear portion comprise one or more layers of fabric. The front portion covers a front part of a pelvic region of the wearer. The rear portion covers a rear part of the pelvic region of the wearer. Lateral edges of the rear portion are connected to lateral edges of the front portion. The crotch portion covers a crotch region of the wearer. The crotch portion comprises one or more of a first layer and a second layer. The first layer is disposed across a mid region of the crotch portion. The second layer comprises a first edge attached to a waist region of the front portion and a second edge attached to a waist region of the rear portion, forming an elongated fabric patch. The second layer further comprises a pair of outer edges folded inwardly over the first layer forming lateral edges of the crotch portion for creating a pair of flaps at the mid region of the crotch portion. The flaps cover one of the extensions of the absorbent pad and prevent the extensions of the absorbent pad from contacting the inner thigh regions of the wearer. In one embodiment, the flaps cover lateral edges of the absorbent pad and prevent the lateral edges from contacting the inner thigh regions of the wearer. The first layer for example, is made of a stiff fabric layer for holding the absorbent pad in place. The second layer of the sanitary undergarment prevents staining of the outer garment at the inner thigh region. Furthermore, the second layer of the sanitary undergarment prevents staining and chafing of the sanitary undergarment at the inner thigh region.

The crotch portion, for example, accommodates the absorbent pad on top of the first layer. In an embodiment, the first layer and the second layer of the crotch portion are made of breathable and leak-proof material. In another embodiment, the second layer of the crotch portion is made of an absorbing material for absorbing the body fluid and for keeping the wearer dry on the inside. The second layer of the crotch portion made of the absorbing material and acts as a receiving pouch for excess body fluid. The first layer of the crotch portion holds the absorbent pad in place and receives extensions of the absorbent pad. The extensions are flipped below the first layer along lateral sides of the first layer. In one embodiment, the first layer is made of an absorbing material and acts as a receiving pad for leakages from a tampon. The second layer of the crotch portion prevents chafing of the skin at the inner thigh region of the wearer. One or more fabric strips are for example, disposed across the first layer for holding the first layer in place. In an embodiment of the sanitary undergarment, the second layer of the crotch portion encapsulates the first layer. In another embodiment of the sanitary undergarment, the pair of outer edges of the second layer folded inwardly over the first layer are stitched along the lateral edges of the crotch portion, except for the lateral edges in the mid region of the crotch portion, for creating the flaps. The flaps are held in place at the mid region of the crotch portion using, for example, a fastener, one or more fabric strips disposed across the first layer, and an elastic material attached to the flaps.

The front portion and the rear portion of the fabric body comprise one or more layers of fabric. The fabric is, for example, breathable and leak-proof for blocking flow of the body fluid through the fabric body to the outer region of the sanitary undergarment. Furthermore, the fabric blocks flow of the body fluid through the fabric body to an outer garment of the wearer. In an embodiment, the fabric body comprises a first fabric layer, a second laminate layer, and a third fabric layer. The first fabric layer is made of an absorbent material for absorbing leaked-out body fluid. The first fabric layer comes in contact with the pelvic region of the wearer. In another embodiment the first fabric layer maintains dryness of a contact surface of the wearer's body. The first fabric layer is treated with stain proof or stain resistant materials for easy removal of stains. The second laminate layer is sandwiched between the first fabric layer and the third fabric layer. The second laminate layer is, for example, made of a breathable and leak-proof laminate material for preventing leakage of the absorbed body fluid to the third fabric layer. The first fabric layer and the third fabric layer are, for example, made of conventional fabrics used for constructing undergarments. The third fabric layer is exposed to the wearer's outer garment. In another embodiment, the fabric body comprises a single layer of a leak-proof, breathable and a stain proof fabric. The single layer, which is breathable, is subjected to technologies, for example, nanotechnology to provide a dry feeling to the wearer and prevent staining of the wearer's outer garment.

The layers of the fabric body are made of, for example, cotton, polyester, cotton and polyester mix, cotton blends, polyester blends, synthetics, synthetic blends with different treatments or lamination. One or more of the layers of the fabric body are, for example, treated with an anti-microbial substance for preventing occurrence of odors and infections on the wearer's body. Furthermore, one or more layers of the fabric body are, for example, subjected to an odor resistance treatment for preventing odor from, for example, a soiled absorbent pad.

In another embodiment of the sanitary undergarment, the fabric body at the crotch portion is disposed across the leg openings and is stitched at the leg opening regions. In an embodiment, the crotch portion is a contiguous layer of breathable leak-proof fabric extending from a waist region of the front portion to a waist region of the rear portion without any stitches. This embodiment is suitable for use along with the absorbent pad or the tampon.

An upper edge of the front portion and an upper edge of the rear portion define a waist opening. A pair of lower edges of the front portion and a pair of lower edges of the rear portion define a thigh opening. The lower edges of the front portion and the rear portion are extended to cover inner thigh regions of the wearer. In an another embodiment, an elastic is provided at the thigh openings and at the waist opening to ensure the wearer a snug fit of the sanitary undergarment, not allowing body fluid to escape through the sanitary undergarment. The fabric body made of one or more layers of the breathable leak-proof material blocks flow of the body fluid of the wearer outside the sanitary undergarment, prevents staining of the outer garment on the front part of the pelvic region, the rear part of the pelvic region, the crotch part, and the inner thigh regions of the wearer, and provides comfort to the wearer by allowing air permeability.

In another embodiment of the sanitary undergarment, the front portion and the rear portion together form a contiguous fabric without seams. In yet another embodiment of the sanitary undergarment, the front portion, the crotch portion, and the rear portion are stitched together, forming one or more seams. In an embodiment, the sanitary undergarment comprises a boxer brief structure for preventing staining at the crotch region of the outer garment. The layers in the sanitary undergarment are made with stain-proof and stain repellent fabrics for ensuring that any stains that are formed on the layers are easily washed off without creating any permanent stains.

The seams of the of the sanitary undergarment are for example sealed using a water-proof garment grade sealant for preventing leakage of the body fluid of the wearer to the outer garment.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
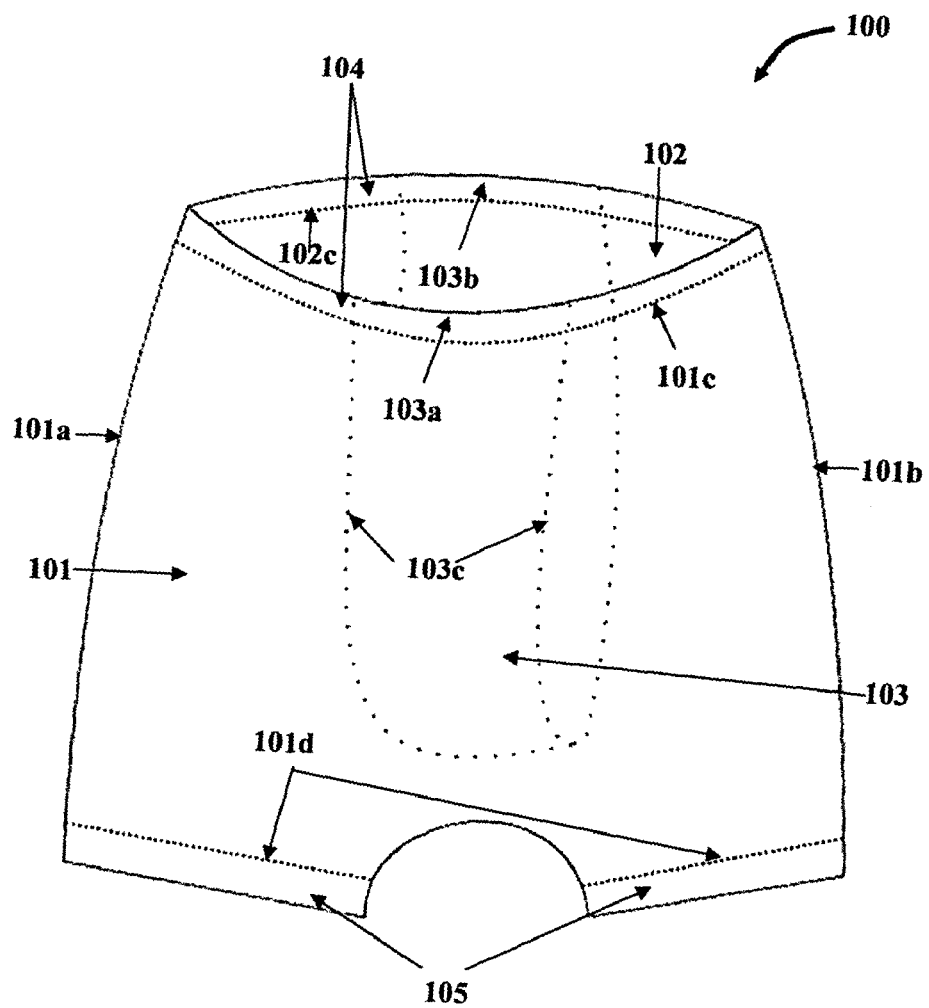
FIG. 1 exemplarily illustrates a boxer brief construction of a sanitary undergarment for preventing staining of an outer garment of a wearer by a body fluid of the wearer.

FIG. 1 exemplarily illustrates a sanitary undergarment 100 for preventing staining of an outer garment of a wearer by a body fluid of the wearer. The sanitary undergarment 100 disclosed herein comprises a fabric body comprising one or more layers made of a breathable leak-proof material for blocking the flow of the body fluid through the fabric body.

Figure 4:
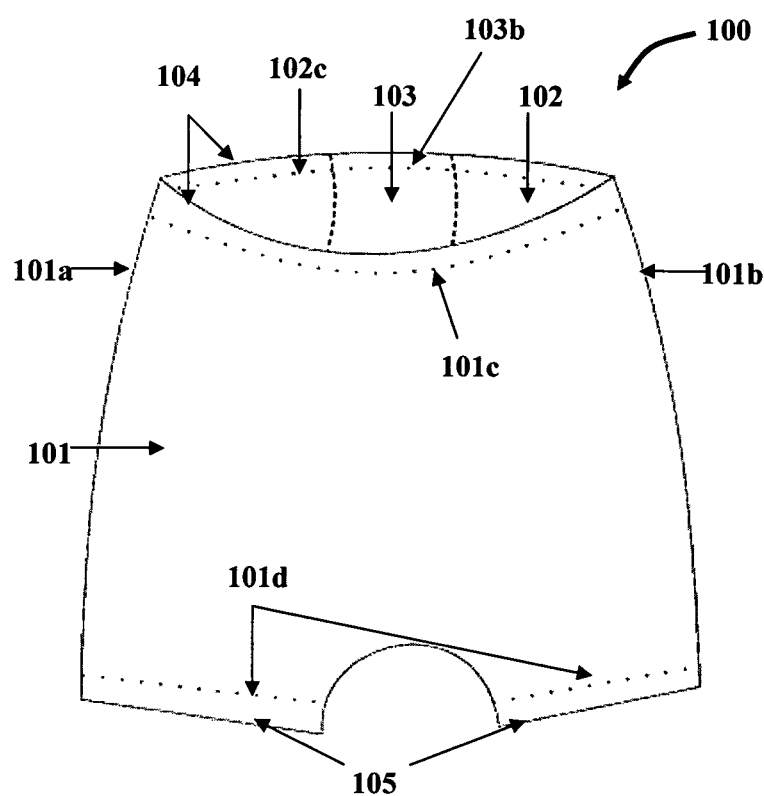
FIG. 4 exemplarily illustrates a front view of the boxer brief construction of the sanitary undergarment.
Figure 5:
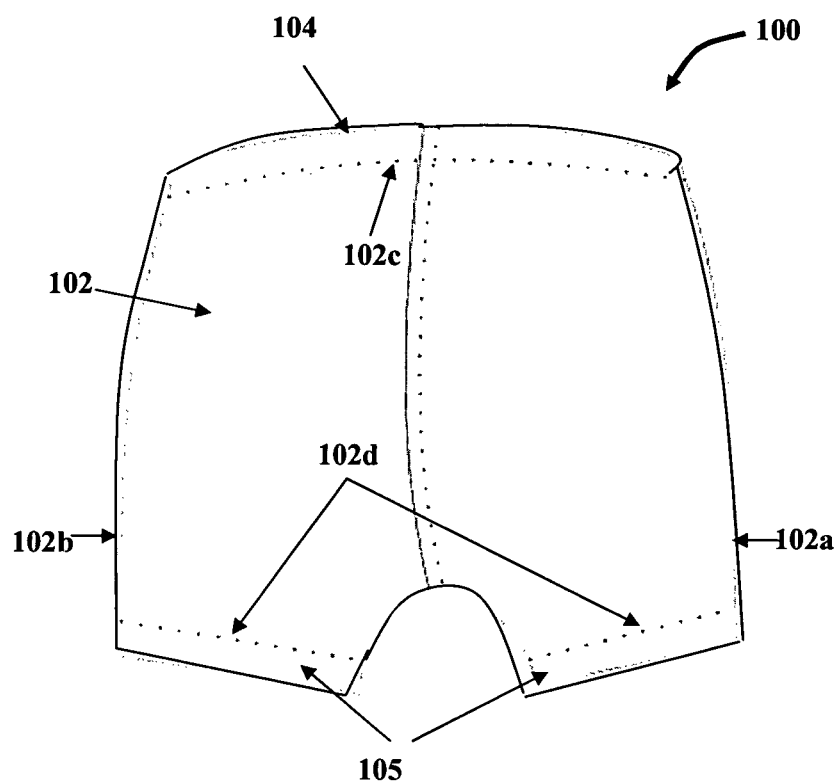
FIG. 5 exemplarily illustrates a rear view of the boxer brief construction of the sanitary undergarment with stitches in the rear portion.
Figure 6:
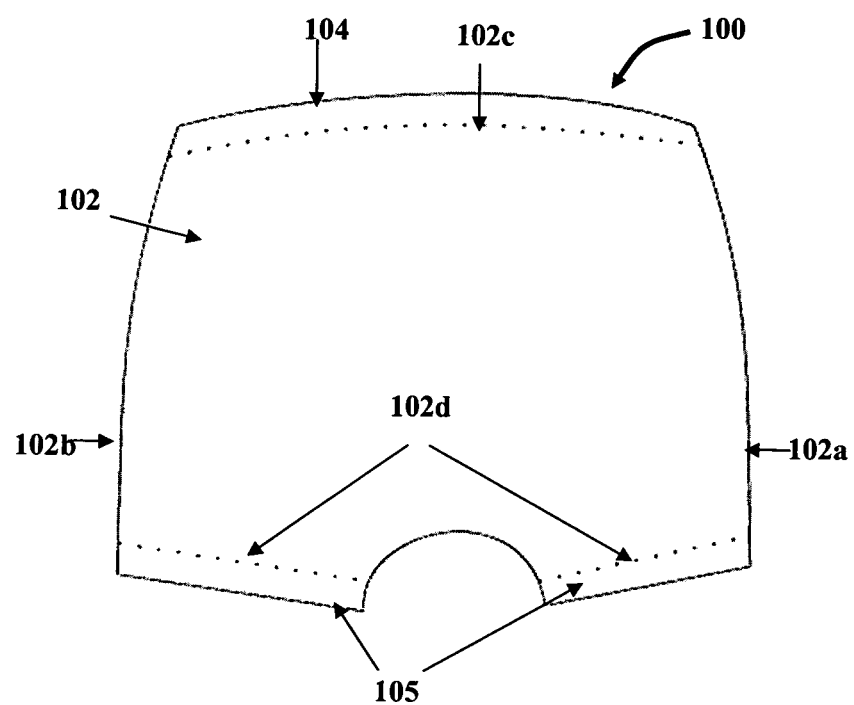
FIG. 6 exemplarily illustrates the rear view of the boxer brief construction of the sanitary undergarment without stitches in the rear portion.

The sanitary undergarment 100 comprises a front portion 101, a crotch portion 103, a rear portion 102, a waist opening 104, and thigh openings 105. The front portion 101 covers a front part of a pelvic region of the wearer. The front portion 101 covers, for example, the wearer's belly. A front view of the sanitary undergarment 100 illustrating the front portion 101 is exemplarily illustrated in FIG. 4. The rear portion 102 covers a rear part of the pelvic region of the wearer. A rear view of the sanitary undergarment 100 illustrating the rear portion 102 is exemplarily illustrated in FIG. 5. The sanitary undergarment 100 in FIG. 5 comprises a stitch running through the length of the rear section and at various other selected regions on the sanitary undergarment 100. A rear view of the sanitary undergarment 100 without stitches in the rear portion 102 is exemplarily illustrated in FIG. 6.

The rear portion 102 covers, for example, the backside of the pelvic region. The lateral edges 102a and 102b of the rear portion 102 are connected to lateral edges 101a and 101b of the front portion 101. The upper edge 101c of the front portion 101 and the upper edge 102c of the rear portion 102 define a waist opening 104. The waist opening 104 is, for example, provided with stretchable elastic lining for gripping the sanitary undergarment 100 firmly around the wearer's waist region. Additionally, the waist opening 104 is, for example, provided with a substantially broad elastic band for covering the entire belly region and the corresponding back region of the wearer. The elastic band provides, for example, additional support, alleviates stomach cramps, prevents back ache, and reduces bloating of the belly.

The lateral edges 103c of the crotch portion 103, the lower edges 101d and 102d of the front portion 101 and the rear portion 102 define thigh openings 105. The thigh openings 105 are, for example, provided with the stretchable elastic lining for firmly gripping the sanitary undergarment 100 around the wearer's thigh region. The sanitary undergarment 100 is, for example, pulled upward for being worn by inserting legs of the wearer in the thigh openings 105.

The lateral edges 103c of the crotch portion 103 and the lower edges 101d and 102d of the front portion 101 and rear portion 102 respectively are extended to cover the inner thigh regions of the wearer. The extension of the lateral edges 103c of the crotch portion 103 and the lower edges 101d and 102d of the front portion 101 and the rear portion 102 renders, for example, a boxer brief design to the sanitary undergarment 100. The boxer brief design provides comfort and protection from stains. The extension of the lateral edges 103c of the crotch portion 103 and the lower edges 101d and 102d of the front portion 101 and the rear portion 102 ensures any leakage of the body fluid is arrested within the sanitary undergarment 100 and prevents the wearer's outer garment from being stained. The fabric body made of the multiple layers of the breathable leak-proof material blocks flow of the body fluid of the wearer outside the sanitary undergarment 100 and prevents staining on the outer side of the sanitary undergarment 100, particularly on the front part of the pelvic region, the rear part of the pelvic region, the crotch region, and the inner thigh regions of the wearer, and provides comfort to the wearer by allowing air permeability. The sanitary undergarment 100 is, for example, washable and reusable. Furthermore, any needle holes formed during construction of the sanitary undergarment 100 is sealed with, for example, a water-proof garment grade sealant. The layers of the fabric body are also, for example, treated with a water-proof material. Treatments involving nanotechnology is, for example, used to achieve water-proof properties.

Figure 2A:
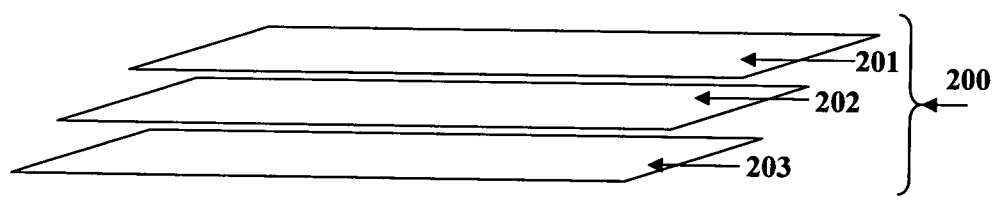
FIG. 2A exemplarily illustrates three layered structure of a fabric body used to construct the sanitary undergarment.

The boxer brief construction of the sanitary undergarment 100 prevents staining at the inner thigh region of the wearer. In this embodiment, the front portion 101 and the rear portion 102 of the fabric body 200 comprise a first fabric layer 201, a second laminate layer 202, and a third fabric layer 203. The three layered structure of the fabric used to construct the sanitary undergarment 100 is exemplarily illustrated in FIG. 2A. For the purposes of illustration, the detailed description refers to a first fabric layer 201, a second laminate layer 202, and a third fabric layer 203; however the scope of the fabric body 200 is not limited to the first fabric layer 201, the second laminate layer 202, and the third fabric layer 203 but may be extended to include single layer or multiple layers comprising one or more of an absorbing property, a leak-proof property and a breathable property. The first fabric layer 201 is, for example, made of an absorbent material for absorbing leaked-out body fluid. The first fabric layer 201 comes in contact with the pelvic region of the wearer. The first fabric layer 201 is, for example, an absorbing, dry and stain proof layer. The first fabric layer 201 maintains dryness of a contact surface of the wearer's body. Furthermore, any stains due to leakage of the body fluid on the first fabric layer 201 are washable since the first fabric layer 201 is made of a stain proof material. The second laminate layer 202 is sandwiched between the first fabric layer 201 and a third fabric layer 203. The second laminate layer 202 is made of a breathable leak-proof material and prevents leakage of the absorbed body fluid to the third fabric layer 203.

Figure 3:
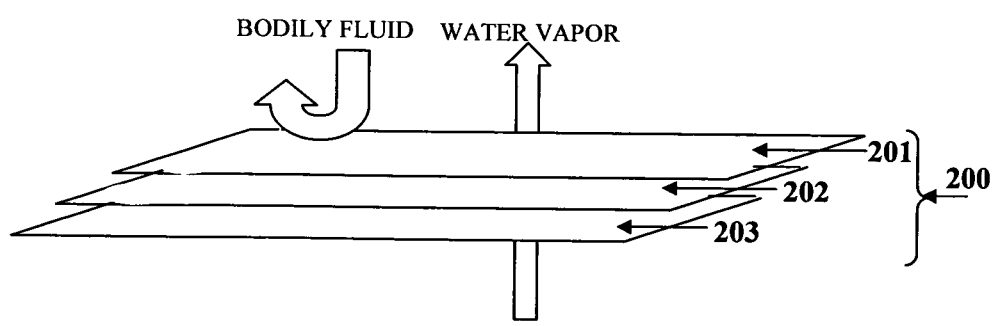
FIG. 3 exemplarily illustrates properties of the fabric.

The second laminate layer 202 sandwiched between the first fabric layer 201 and the third fabric layer 203. The second laminate layer 202 prevents the flow of the body fluid to the third fabric layer 203 in case of a leakage in the first fabric layer 201 and thus prevents staining of the third fabric layer 203. The first fabric layer 201 and the third fabric layer 203 are, for example, made of a stain resistant, stain release or stain proof fabric which facilitates easy removal of the stains on the sanitary undergarment 100. The second laminate layer 202 does not come in contact with the body of the wearer and hence prevents discomfort to the wearer. The second laminate layer 202 is air permeable and allows water vapor to pass through the fabric body 200 as illustrated in FIG. 3, but prevents leakage of the body fluid outside the fabric body 200. Furthermore, the second laminate layer 202 of the sanitary undergarment 100 prevents rashes and odor by allowing air permeability.

Figure 2B:
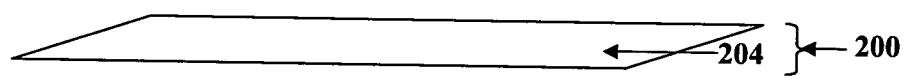
FIG. 2B exemplarily illustrates a single layered structure of the fabric body.

The third fabric layer 203 is made of a conventional fabric and is exposed to the outer garment of the wearer. The third fabric layer 203 is exposed to the wearer's outer garment. One or more of the multiple layers are subjected to, for example, an anti-microbial treatment for preventing odor, rashes and infections on the wearer's body. Furthermore, one or more of the multiple layers of the fabric body 200 are subjected to, for example, an odor resistant treatment for preventing odor from a soiled absorbent pad. In another embodiment, the fabric body 200 comprises a single layer 204 of breathable fabric, treated with a leak-proof technology to prevent staining of the wearer's outer garment. The single layered structure of the fabric body 200 is exemplarily illustrated in FIG. 2B. The single layer 204 is, for example, a breathable material such as cotton fabric subjected to, for example, nanotechnology treatment.

The layers of the fabric body 200 are made of, for example knitted cotton, polyester, cotton and polyester mix, cotton blends, polyester blends, synthetics, synthetic blends with a coating, lamination or fabric treatments etc. The synthetics used are, for example, acetate, polyamides such as nylon, olefins such as polypropylene and polyethylene, spandex, etc. The coating, lamination or treatments on the fabric body 200 prevent leakage of the body fluid outside the sanitary undergarment 100.

Figure 7A:
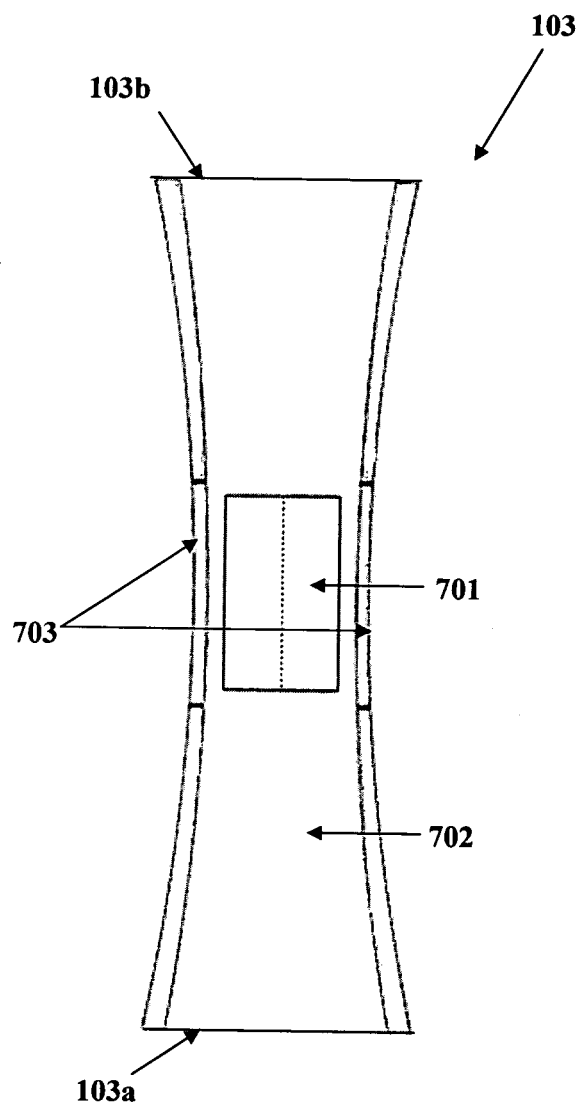
FIGS. 7A-7E exemplarily illustrate various embodiments of the crotch portion of the sanitary undergarment.

The crotch portion 103 covers a crotch region of the wearer. The crotch portion 103 comprises one or more of a first layer and a second layer. The first layer is disposed across a mid region of the crotch portion 103. The first layer is made of an absorbing, breathable and leak-proof fabric. The absorbent pad is fixed upon the first layer. If a tampon is used, the first layer receives excess body fluid leaked out from the tampon. The second layer comprises a first edge 103a attached to a waist region of the front portion 101 and a second edge 103b attached to a waist region of the rear portion 102, forming an elongated fabric patch as exemplarily illustrated in FIGS. 7A-7E and 8. The second layer further comprises a pair of outer edges folded inwardly forming lateral edges 103c of the crotch portion 103 for creating a pair of flaps at the mid region of the crotch portion 103 as illustrated in FIG. 7A. The flaps 703 cover a pair of extensions of the absorbent pad 801. If the absorbent pad 801 does not comprise extensions, the flaps 703 cover the lateral edges of the absorbent pad 801 and prevent the absorbent pad 801 from contacting the inner thigh regions of the wearer. The second layer 702 of the sanitary undergarment 100 prevents staining of the outer garment at the crotch region of the wearer. In an embodiment of the sanitary undergarment, the crotch portion 103 comprises multiple layers of fabric. In another embodiment of the sanitary undergarment, the first layer 701 and the second layer 702 of the crotch portion are stitched together at selected regions.

Figure 11:
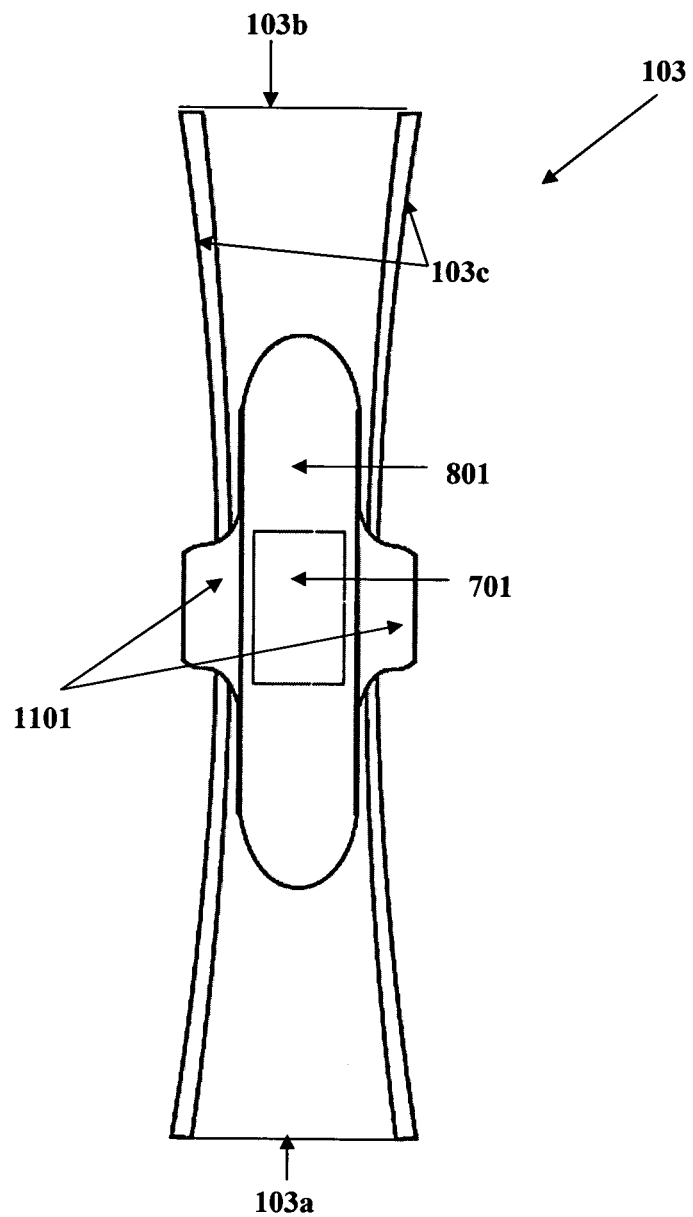
FIG. 11 exemplarily illustrates the crotch region of the sanitary undergarment comprising the absorbent pad attached to the first layer of the crotch portion.
Figure 12:
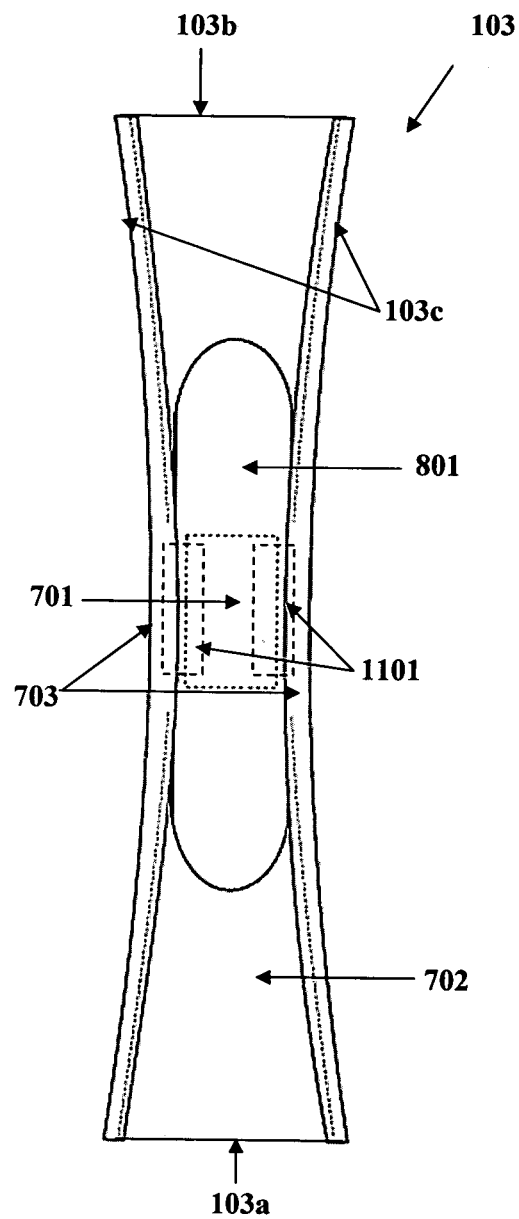
FIG. 12 exemplarily illustrates the crotch region of the sanitary undergarment comprising the absorbent pad attached to the first layer and the extensions of the absorbent pad flipped into the flaps.

The crotch portion 103 accommodates an absorbent pad 801. The first layer 701 and the second layer 702 are made of, for example, absorbing, breathable and leak-proof material. In yet another embodiment, each of the first layer 701 and the second layer 702 are made of a single layer of leak-proof fabric. In yet another embodiment, the first layer 701 of the crotch portion 103 is made of an absorbing material for absorbing the body fluid and keeping the wearer dry on the inside. The second layer 702 of the crotch portion 103 is made of a breathable and leak-proof material and acts as a receiving pouch for excess body fluid. The first layer 701 of the crotch portion 103 holds the absorbent pad 801 in place and receives extensions 1101 of the absorbent pad 801. The absorbent pad 801 is positioned on the first layer 701 as illustrated in FIG. 11. The extensions 1101 are flipped below the first layer 701 along lateral sides of the first layer 701 as illustrated in FIG. 12. The extensions 1101 are covered by the flaps 703 and the flaps 703 are held in place by fasteners. The flaps 703 of the second layer 702 of the absorbent pad 801 prevent staining of the outer garment of the wearer. Further, the flaps 703 also prevent chafing of the skin at the inner thigh region of the wearer. The sanitary undergarment 100 is also used along with, for example, absorbent pads without extensions, tampon, reusable fabric pads, menstrual cups, other form of hygiene product, etc.

Figure 7B:
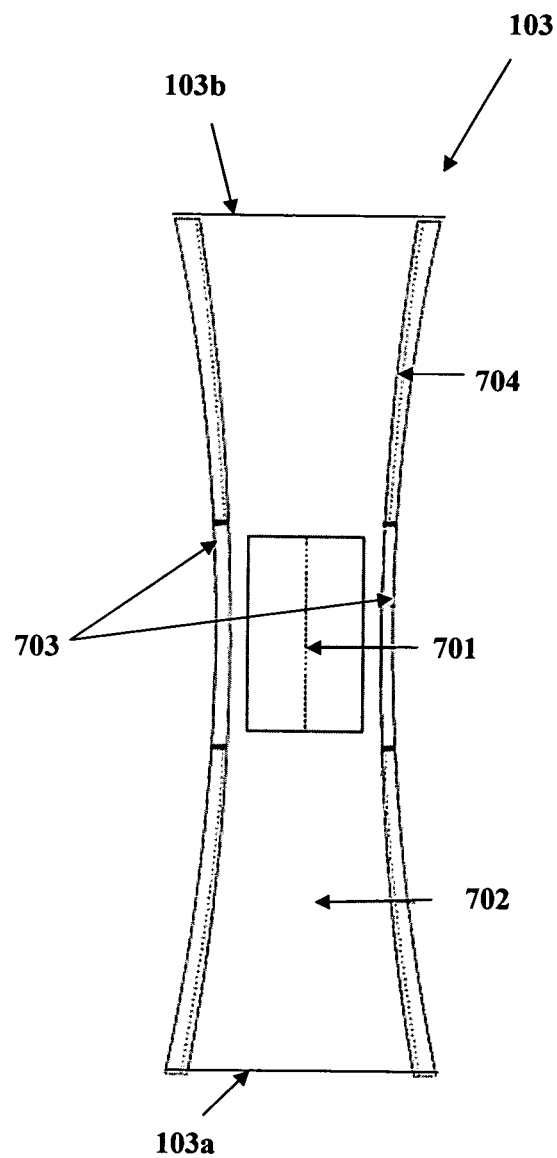
Figure 7C:
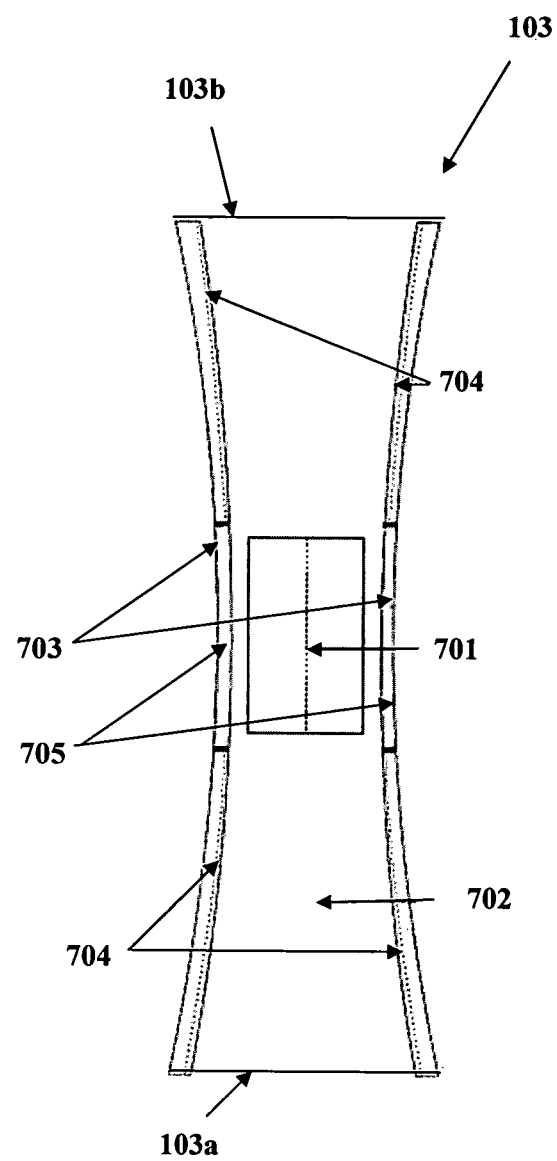

The second layer 702 of the crotch portion 103 prevents chafing of the skin at the inner thigh region of the wearer. In an embodiment of the sanitary undergarment 100, the second layer 702 of the crotch portion 103 encapsulates the first layer 701. In another embodiment of the sanitary undergarment 100, the pair of outer edges of the second layer 702 folded inwardly are stitched at selected regions for creating and holding flaps 703 and for preventing chafing of the skin at the inner thigh region of the wearer. In yet another embodiment, the stitches 704 run along the lateral edges 103c of the crotch portion 103 except for the lateral edges 103c in the mid region of the crotch portion 103 for creating the flaps 703 as illustrated in FIG. 7B. The flaps 703 covers the flipped extensions 1101 of the absorbent pad 801. In one embodiment of the absorbent pad, if the absorbent pad 801 does not comprise extensions 1101, the flaps 703b cover lateral edges of the absorbent pad 801. The flaps 703 are held in place using, for example, a fastener 705 as illustrated in FIG. 7C. The fastener 705 is, for example, Velcro® or washable and reusable fabric grade glue, etc.

Figure 7D:
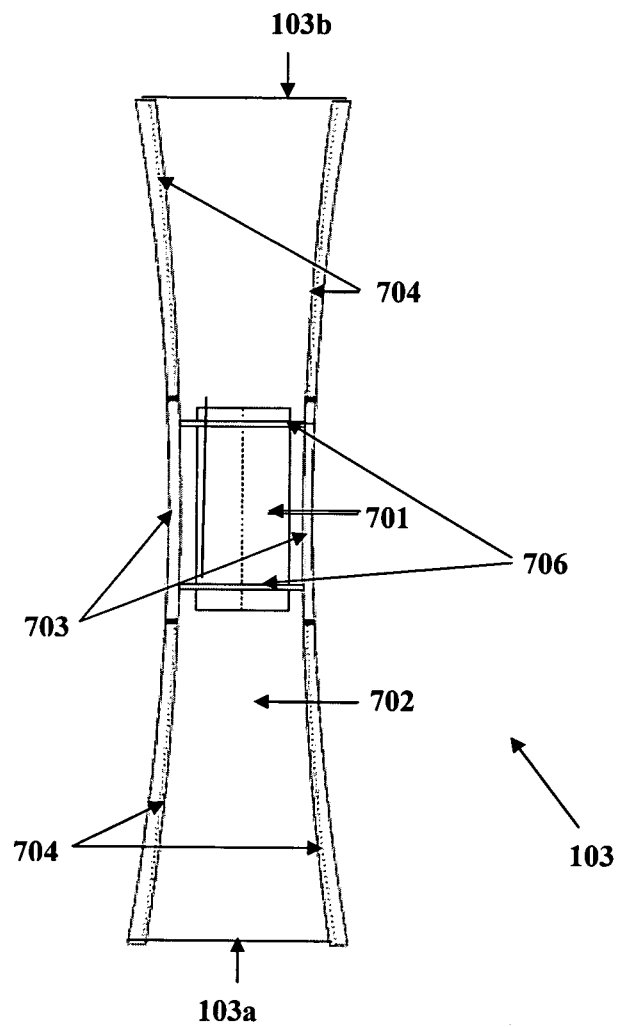
Figure 7E:
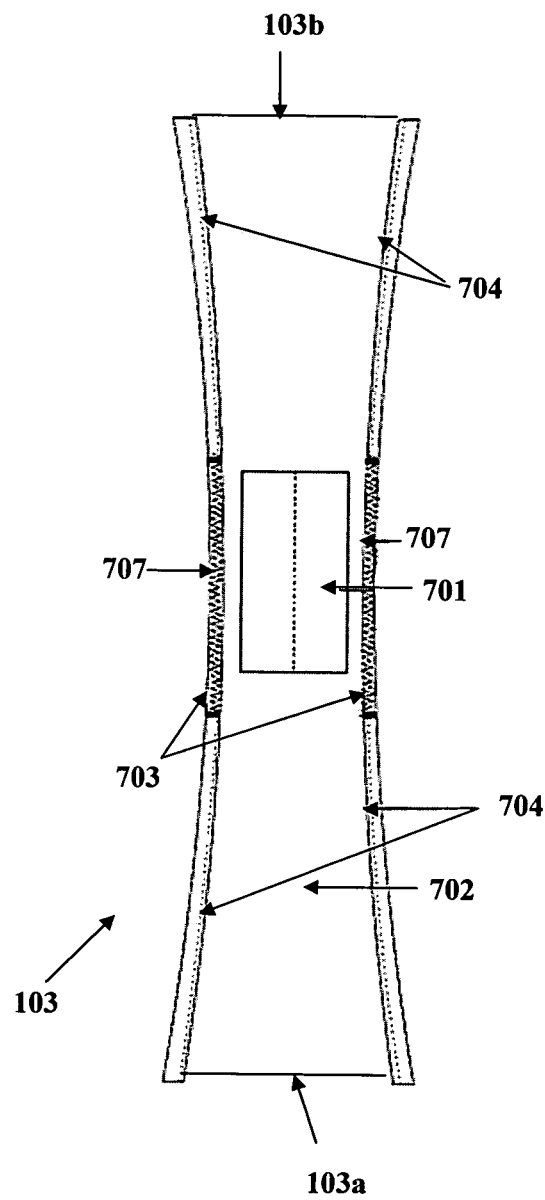
Figure 8:
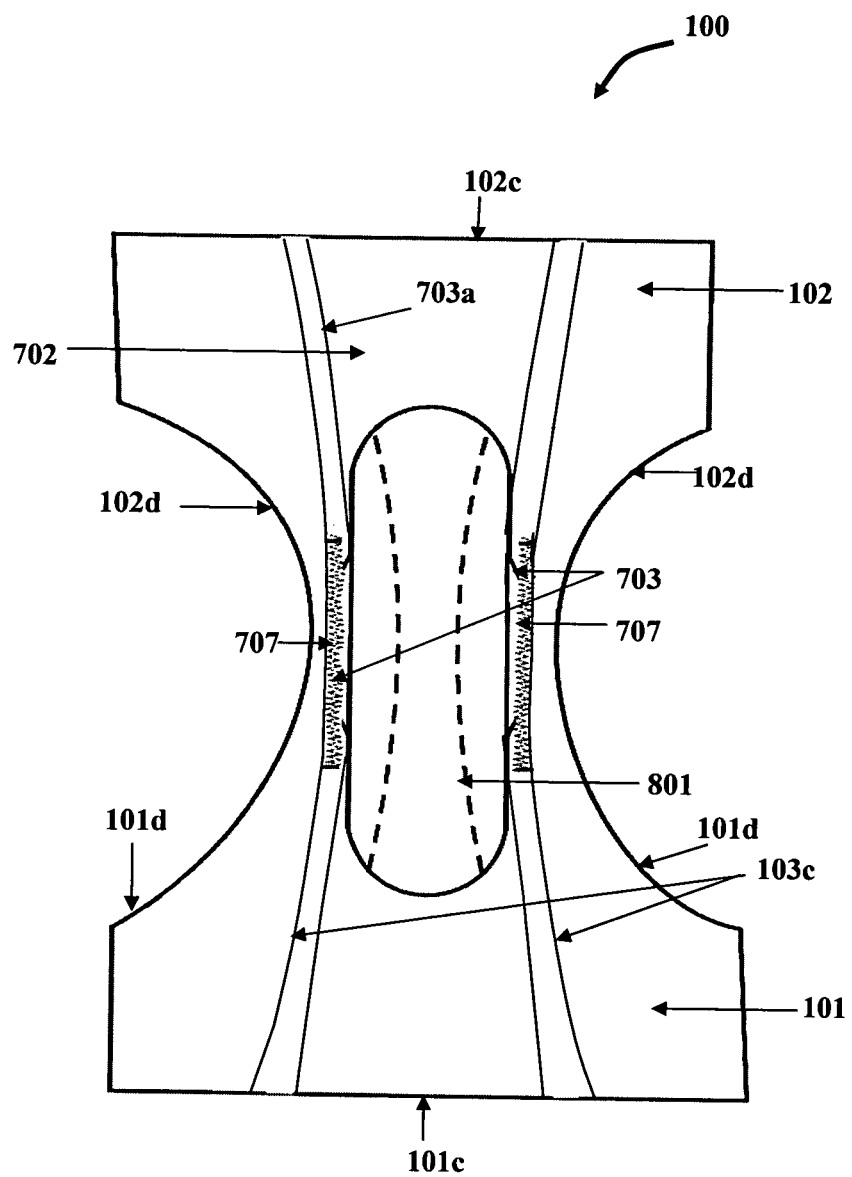
FIG. 8 exemplarily illustrates an open view of the sanitary undergarment comprising an absorbent pad disposed on crotch portion.

In yet another embodiment, the flaps 703 are fastened using one or more fabric strips 706 disposed across the first layer 701 for holding the flaps in place as illustrated in FIG. 7D. In yet another embodiment, the flaps 703 are fastened using an elastic material 707 attached to the flaps 703 as illustrated in FIG. 7E. In yet another embodiment a combination of one or more of the fastener, the fabric strips, the elastic material and the stitches 704 running at selected regions on the outer edges of the second layer 702 is used for fastening the flaps 703.

The second layer 702 is made of soft, absorbing fabric material for preventing discomfort and rashes. The first layer 701 and the second layer 702 ensure that the absorbent pad 801 is always accommodated in the crotch portion 103 of the sanitary undergarment 100. The crotch portion 103 of the sanitary undergarment 100 comprising an absorbent pad 801 disposed on the crotch portion 103 is exemplarily illustrated in FIG. 8.

Figure 9:
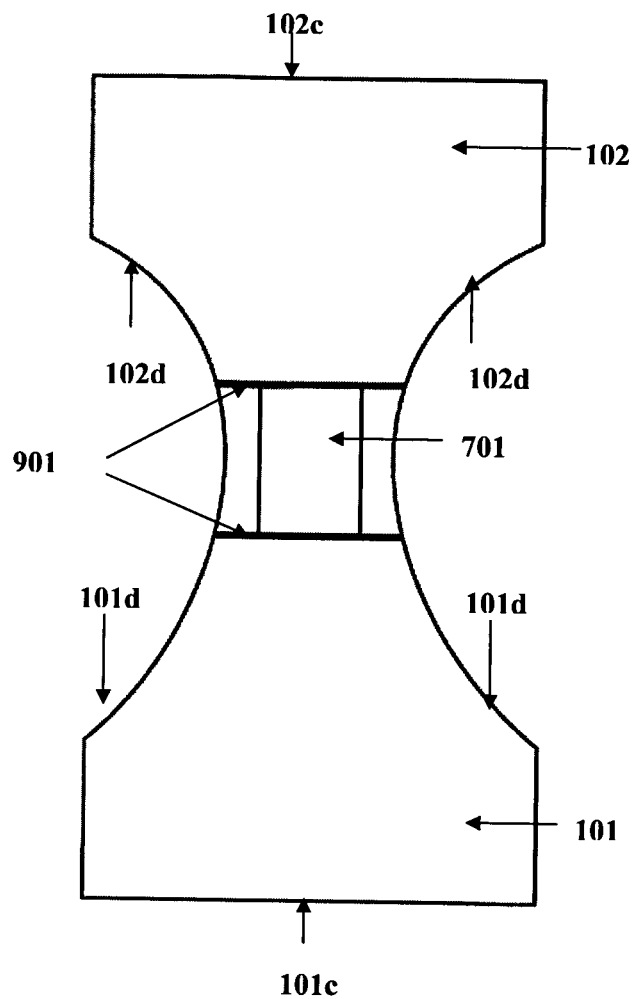
FIG. 9 exemplarily illustrates yet another embodiment of the sanitary undergarment comprising a first layer at the mid region of the crotch portion.
Figure 10:
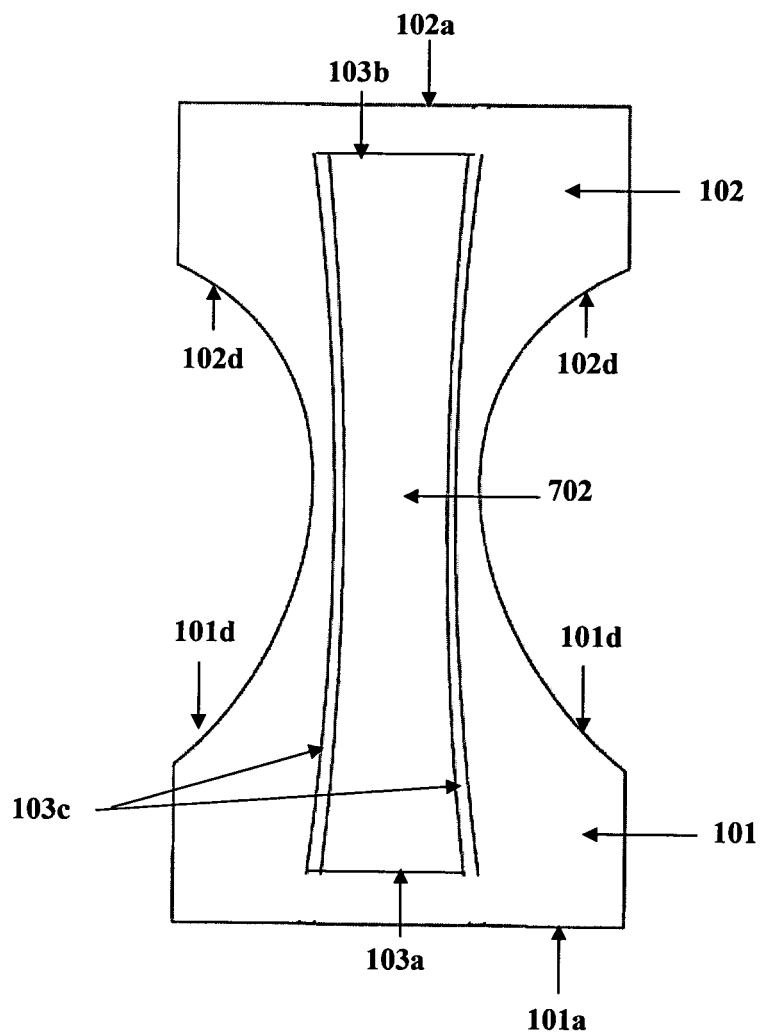
FIG. 10 exemplarily illustrates yet another embodiment of the sanitary undergarment comprising a second layer alone in the crotch portion.

In an embodiment, the crotch portion 103 is a contiguous layer of breathable leak-proof fabric extending from the upper edge 101c of the front portion 101 to the upper edge 102c of the rear portion 102 and attached to the upper edge 101c of the front portion 101 to the upper edge 102c of the rear portion 102 without any stitches. This embodiment is suitable for use with an absorbent pad 801 or a tampon. In another embodiment of the sanitary undergarment 100, the front portion 101 and the rear portion 102 together form a contiguous fabric without seams. In yet another embodiment of the sanitary undergarment 100, the front portion 101, the crotch portion 103, and the rear portion 102 are stitched together forming one or more seams. The seams are, for example, sealed using the water-proof garment grade sealant. In yet another embodiment the sanitary undergarment 100 comprises a boxer brief structure for preventing staining at the crotch region on the outer garment. In yet another embodiment, the crotch portion 103 comprises only the first layer 701 for accommodating the absorbent pad 801 as illustrated in FIG. 9. One or more fabric strips 901 are disposed across the first layer 701 for holding the first layer 701 in place. In yet another embodiment, the crotch portion 103 comprises only the second layer 702 for accommodating the absorbent pad 801 as illustrated in FIG. 10.

Figure 13:
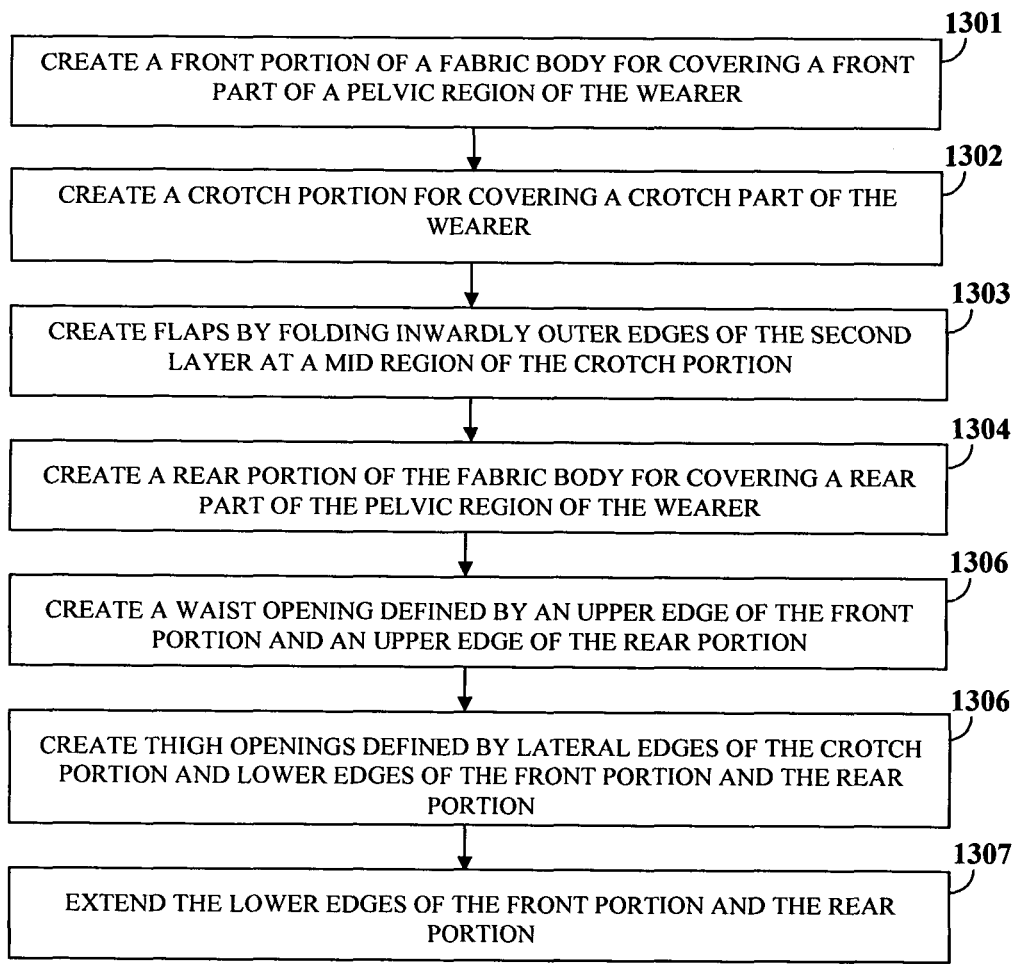
FIG. 13 illustrates a method of constructing a sanitary undergarment for preventing staining of the outer garment of the wearer by the body fluid of the wearer.

FIG. 13 illustrates a method of constructing a sanitary undergarment 100 for preventing staining of an outer garment of a wearer by a body fluid of the wearer. A front portion 101 of a fabric body 200 is created 1301 for covering a front part of a pelvic region of the wearer. A crotch portion 103 is created 1302 for covering a crotch region of the wearer. The crotch portion comprises one or more of a first layer 701 and a second layer 702. The embodiments of the first layer 701 and the second layer 702 are explained in the detailed description of FIG. 1. In an embodiment, a contiguous layer of fabric is used for creating the crotch portion 103. The contiguous layer extends from the front portion 101 to the rear portion 102 of the sanitary undergarment 100 without any stitches. A pair of flaps 703 is created 1303 at a mid region of the crotch portion 103 by folding inwardly outer edges of the second layer forming lateral edges 103c of the crotch portion 103.

The flaps 703 are created for covering a pair of edges of extensions 1101 of an absorbing pad 801 for preventing chafing of skin of the wearer at an inner thigh region. In one embodiment, if the absorbent pad does not comprise extensions 1101, the flaps 703 hold the absorbent pad 801 in place by covering the lateral edges of the absorbent pad 801. A rear portion 102 of the fabric body 200 is created 1304 for covering a rear part of the pelvic region of the wearer. A pair of lateral edges 102a and 102b of the rear portion 102 are connected to a pair of lateral edges 101a and 101b of the front portion 101. The front portion 101 and rear portion 102 of the fabric body 200 are created by creating a first fabric layer 201, a second laminate layer 202, and a third fabric layer 203. The first fabric layer 201 is made of an absorbent material for absorbing leaked-out body fluid. The first fabric layer 201 comes in contact with the pelvic region of the wearer. A second laminate layer 202 is sandwiched between the first fabric layer 201 and a third fabric layer 203. The second laminate layer 202 is made of a breathable leak-proof material for preventing leakage of the absorbed body fluid to the third fabric layer 203. The third fabric layer 203 is exposed to the outer garment of the wearer. One or more of the first fabric layer 201, the second laminate layer 202, the third fabric layer 203, the first layer 701, and the second layer 702 are subjected to an anti-microbial treatment for preventing odors and infections on body of the wearer. In yet another embodiment, one or more of the first fabric layer 201, the second laminate layer 202, the third fabric layer 203, the first layer 701, and the second layer 702 are subjected to an odor resistant treatment for preventing odor from a soiled absorbent pad. A waist opening 104 defined by an upper edge 101c of the front portion 101 and upper edge 102c of the rear portion 102 is created 1305. A pair of thigh openings 105 defined by a pair of lower edges 101d of the front portion 101 and a pair of lower edges 102d of the rear portion 102 are created 1306. The lateral edges 103c of the crotch portion 103 and the lower edges 101d of the front portion 101 and the lower edges 102d of the rear portion 102 are extended 1307 to cover the inner thigh regions of the wearer, thereby constructing the sanitary undergarment 100. In yet another embodiment, a single fabric layer that is breathable and leak-proof is used for creating the front portion 101 and the rear portion 102 of the sanitary undergarment. Further, the breathable and leak-proof single fabric layer prevents staining of the outer garment of the wearer by not allowing the body fluid of the wearer from passing through and reaching the outer surface of the sanitary undergarment.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

I claim:

1. A sanitary undergarment for preventing staining on an outer garment by a body fluid of a wearer, comprising:
    a fabric body comprising:
        a front portion for covering a front part of a pelvic region of said wearer having a waist region;
        a rear portion for covering a rear part of said pelvic region of the wearer having a waist region, wherein lateral edges of said rear portion are connected to lateral edges of said front portion;
        said front portion and said rear portion of the fabric body comprising:
            a first fabric layer made of an absorbent material for absorbing the body fluid, wherein said first fabric layer comes in contact with the pelvic region of the wearer;
            a second laminate layer sandwiched between the first fabric layer and a third fabric layer, wherein said second laminate layer is made of a breathable fluid leak-proof material for preventing leakage of said absorbed body fluid to said third fabric layer; and
            the third fabric layer exposed to the outer garment of the wearer;
        a crotch portion for covering a crotch region of the wearer, comprising at least a fourth crotch layer and a fifth crotch layer, wherein said fourth crotch layer is disposed across a mid region of said crotch portion and said fifth crotch layer comprising a first edge attached to a waist region of the front portion and a second edge attached to a waist region of the rear portion; and
        wherein said fourth crotch layer is made of an absorbing material for keeping the wearer dry on the inside, and said fifth crotch layer is made of an absorbing fluid leak-proof material and acts as a receiving pouch for excess body fluid;
        the said fifth crotch layer forming an elongated fabric patch comprising a pair of outer edges, wherein said pair of outer edges are folded inwardly over the fourth crotch layer thereby forming lateral edges of the crotch portion for creating flaps at said mid region of the crotch portion, whereby the said fifth crotch layer encapsulates the fourth crotch layer;
        a waist opening disposed adjacent the waist regions defined by an upper edge of the front portion and an upper edge of the rear portion; and
        thigh openings defined by a pair of lower edges of the front portion and a pair of lower edges of the rear portion, wherein said lower edges of the front portion and the rear portion are extended to cover inner thigh regions of the wearer;
    whereby the fabric body, having multiple layers of protection, blocks flow of body fluid of the wearer outside said sanitary undergarment and thereby prevents staining of said outer garment on said front part of the pelvic region, said rear part of the pelvic region, said crotch region, and said inner thigh regions of the wearer, and provides comfort to the wearer by allowing air permeability.

2. The sanitary undergarment of claim 1, wherein the front portion and the rear portion together form a contiguous fabric without seams.

3. The sanitary undergarment of claim 1, wherein the front portion, the crotch portion, and the rear portion are stitched together forming one or more seams.

4. The sanitary undergarment of claim 3, wherein said one or more seams are sealed using a water-proof garment grade sealant for preventing leakage of the body fluid of the wearer to the outer garment.

5. The sanitary undergarment of claim 1 comprising a boxer brief structure, wherein the second layer of the crotch portion of the sanitary undergarment prevents staining of the outer garment at the crotch region of the wearer.

6. The sanitary undergarment of claim 1, wherein the front portion and the rear portion of the fabric body comprise a single layer of fluid leak-proof and breathable fabric layer for preventing staining of the outer garment of the wearer.

7. The sanitary undergarment of claim 1, wherein the fabric body maintains dryness of a contact surface of the body of the wearer.

8. The sanitary undergarment of claim 1, wherein the fourth crotch layer and the fifth crotch layer are made of an absorbing material, wherein said absorbing material is breathable and fluid leak-proof.

9. The sanitary undergarment of claim 1, wherein the fourth crotch layer of the crotch portion holds an absorbent pad in place and receives extensions of said absorbent pad, wherein said extensions are folded inwardly below the fourth crotch layer along lateral sides of the first layer.

10. The sanitary undergarment of claim 9, wherein said flaps cover the extensions of said absorbent pad and prevent said extensions of the absorbent pad from contacting at least a portion of the inner thighs of the wearer.

11. The sanitary undergarment of claim 9, wherein the fourth crotch layer holds an absorbent pad in place, and wherein said flaps cover lateral edges of said absorbent pad and prevent said lateral edges of the absorbent pad from contacting at least a portion of the inner thighs of the wearer.

12. The sanitary undergarment of claim 1, wherein the fifth crotch layer prevents chafing of the skin at least at a portion of the inner thighs of the wearer.

13. The sanitary undergarment of claim 1, wherein one or more fabric strips are disposed across the first layer for holding the first layer in place.

14. The sanitary undergarment of claim 1, wherein the pair of outer edges of the fifth crotch layer are folded inwardly and stitched along said lateral edges of the crotch portion, except for lateral edges in the mid region of the crotch portion for creating said flaps.

15. The sanitary undergarment of claim 1, wherein said flaps are in place at the mid region of the crotch portion for preventing chafing and staining at the inner thigh regions of the wearer, and wherein the flaps are fastened using one or more of: a fastener, fabric strips disposed across the first layer, and an elastic material attached to the flaps.

16. The sanitary undergarment of claim 1, wherein the one or more layers of the fabric body are made of cotton, polyester, cotton and polyester mix, cotton blends, polyester blends, synthetics, and synthetic blends with a coating, lamination or fabric treatments.

17. The sanitary undergarment of claim 1, wherein the one or more layers is subjected to an antimicrobial treatment for preventing odors and infections relating to the body of the wearer.

18. The sanitary undergarment of claim 1, wherein the one or more layers of the fabric body are subjected to an odor resistant treatment for preventing odor from a soiled absorbent pad.

19. The sanitary undergarment of claim 1, wherein said waist opening comprises a waist band.

20. The sanitary undergarment of claim 19, wherein said waist band covers a belly region and a back region at the waist region of the wearer.

21. A method of constructing a sanitary undergarment for preventing staining of an outer garment of a wearer by a body fluid of said wearer, comprising the steps of:
creating a front portion of a fabric body for covering a front part of a pelvic region of the wearer;
creating a crotch portion for covering a crotch region of the wearer, wherein said crotch portion comprises at least a first crotch layer and a second crotch layer, wherein said first crotch layer is disposed across a mid region of the crotch portion and the second crotch layer is formed to encapsulate the first crotch layer, and wherein creating said second crotch layer further comprises creating a contiguous layer of a breathable fluid leak proof fabric extending stitchlessly from an upper edge of the front portion to an upper edge of a rear portion of the fabric body;
creating flaps at the mid region of the crotch portion by inwardly folding outer edges of said second crotch layer, wherein said flaps form lateral edges of the crotch portion;
creating the rear portion of said fabric body for covering a rear part of said pelvic region of the wearer, wherein lateral edges of said rear portion are connected to lateral edges of the front portion;
said creation of said front portion and said rear portion of the fabric body further comprises:
creating a first fabric layer made of an absorbent material for absorbing the body fluid, wherein said first fabric layer comes in contact with the pelvic region of the wearer;
creating a second laminate layer sandwiched between the first fabric layer and a third fabric layer, wherein said second laminate layer is made of a breathable fluid leak-proof material for preventing leakage of said absorbed body fluid to said third fabric layer; and
wherein the third fabric layer is positioned and oriented to be exposed to the outer garment of the wearer;
creating a waist opening defined by an upper edge of the front portion and upper edge of the rear portion;
creating thigh openings defined by a pair of lower edges of the front portion and a pair of lower edges of the rear portion; and
extending said lateral edges of the crotch portion and said lower edges of the front portion and the rear portion to cover at least a portion of the inner thighs of the wearer.

* * * * *